United States Patent [19]

Butler et al.

[11] Patent Number: 4,619,937

[45] Date of Patent: Oct. 28, 1986

[54] SATURATED BICYCLIC LACTAM ACIDS AND DERIVATIVES AS COGNITION ACTIVATORS

[75] Inventors: Donald E. Butler, Ann Arbor; Yvon J. L'Italien, Plymouth, both of Mich.

[73] Assignee: Warner-Lambert Company, Morris Plains, N.J.

[21] Appl. No.: 687,181

[22] Filed: Jan. 7, 1985

Related U.S. Application Data

[63] Continuation-in-part of Ser. No. 576,248, Feb. 2, 1984, abandoned.

[51] Int. Cl.$^4$ .................. A61K 31/40; A61K 31/405; C07D 209/34; C07D 209/52
[52] U.S. Cl. .................................. 514/323; 514/339; 514/421; 546/200; 546/272; 546/201; 546/273; 548/452; 548/512
[58] Field of Search ............... 548/452, 512; 546/200, 546/272, 201, 273; 514/323, 339, 421

[56] References Cited

U.S. PATENT DOCUMENTS

| | | | |
|---|---|---|---|
| 2,872,372 | 2/1959 | Hull | 548/486 |
| 4,116,972 | 9/1978 | Kameyama | 548/403 |
| 4,337,265 | 6/1982 | Treasurywala | 548/512 |
| 4,542,148 | 9/1985 | Kuch | 546/273 |

*Primary Examiner*—Sam Rosen
*Assistant Examiner*—Robert Benson
*Attorney, Agent, or Firm*—Jerry F. Janssen

[57] ABSTRACT

Saturated bicyclic lactam acids and their derivatives are useful in the treatment of senility and for reversing amnesia. Pharmaceutical compositions including these compounds, a method of preparing the compounds, and a method of treating senility and reversing amnesia are also disclosed.

13 Claims, No Drawings

SATURATED BICYCLIC LACTAM ACIDS AND DERIVATIVES AS COGNITION ACTIVATORS

CROSS-REFERENCE TO RELATED APPLICATIONS

This application is a continuation-in-part of copending application Ser. No. 576,248 filed Feb. 2, 1984 now abandoned.

BACKGROUND OF THE INVENTION

The present invention relates to compounds and pharmaceutical compositions useful in the treatment of senility and the reversal of amnesia. More particularly, it is concerned with certain saturated bicyclic lactam acids and their derivatives useful as cognition activators, with a method of preparing such compounds, pharmaceutical compositions including these compounds, and a method of treating senility and reversing amnesia.

SUMMARY AND DETAILED DESCRIPTION

In its broadest aspect, the present invention concerns compounds having the structural formula I:

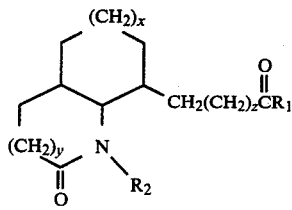

where x is zero, one, two, or three, and y and z are independently zero or one; $R_1$ is selected from —OH, together with the pharmaceutically acceptable metal, ammonium and amine acid addition salts thereof; —OR$_3$, where R$_3$ is alkyl of from one to six carbon atoms, phenyl, or benzyl;

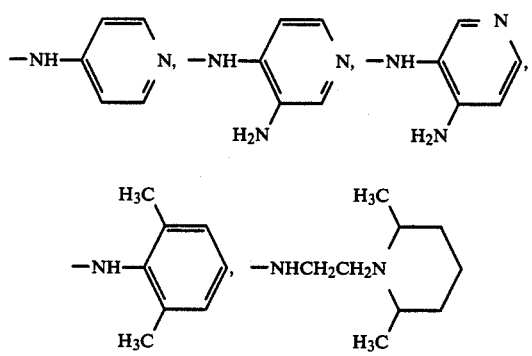

—NHCH$_2$CH$_2$N[CH(CH$_3$)$_2$]$_2$; and —NR$_4$R$_5$ where R$_4$ and R$_5$ are independently hydrogen or alkyl of from one to six carbon atoms or benzyl; and R$_2$ is hydrogen or

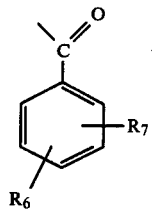

where R$_6$ and R$_7$ are independently hydrogen; halogen; hydroxyl; —OR$_3$ where R$_3$ is as defined above; NR$_8$R$_9$ where R$_8$ and R$_9$ are independently hydrogen, alkyl of from one to six carbon atoms; or when taken together and attached to adjacent carbon atoms are —OCH$_2$O—.

Compounds of the present invention, represented by structure I, comprise a class of structurally related bicyclic fused-ring compounds containing both a lactam ring and a carbocyclic ring with an attached side-chain acetic or propanoic acid group including particular salt, ester, or amide derivatives thereof, and in which the lactam ring nitrogen atom is optionally substituted with benzoyl or substituted-benzoyl.

The present invention contemplates compounds where the carbocyclic ring of structure I shown above may be five-, six-, seven-, or eight-membered, and the lactam ring may be five- or six-membered. Although structurally similar, the compounds of the class encompassed by the present invention possesses somewhat complex nomenclature. The names of the compounds are based in part on the names of the corresponding unsaturated nitrogencontaining fused ring systems.

The compounds of this invention exist in a variety of structural modifications. These include compounds where the carbocyclic ring is five-, six-, seven-, or eight-membered (where x is zero, one, two, or three, respectively, and the lactam ring is five- (y is zero) or six-membered (y is one), and the acid chain is acetic (z is zero) or propanoic (z is one).

In addition, the stereochemistry of the ring juncture between the fused rings may be either cis or trans, and the acetic acid or propanoic acid side-chain may be disposed cis or trans to either or both of the hydrogen atoms at the ring juncture. It should be noted, however, that the possibility for cis and trans ring-juncture (i.e. geometrical) isomerism in the compounds of the present invention is limited to some extent by the difficulty of forming trans-ring junctures in fused-ring systems involving five-membered lactam rings. For example, it is apparently not possible to synthesize structures in which a five-membered lactam ring is joined in a transconfiguration to another five-membered ring.

Further, for those compounds of the present invention in which the molecule has no plane of symmetry, optical isomerism is possible.

The terms "stereoisomers", "stereoisomerism", "optical isomerism", "optical isomers", "geometrical isomerism", and "geometrical isomers" as used throughout this specification and appended claims are those commonly employed by practitioners of the organic chemical art, specifically as defined on pages 1-6 of Eliel, "Stereochemistry of Carbon Compounds," McGraw-Hill, New York, 1962, incorporated herein by reference.

The present invention contemplates all possible ring-size variants, geometrical isomers, and optical isomers of the compounds depicted generically by structural formula I given above.

Also contemplated as falling within the scope of this invention are compounds in which the acetic or propanoic acid function is converted to pharmaceutically acceptable esters, preferably esters derived from alcohols containing from one to six carbon atoms, phenol, and benzyl alcohol.

By the term "alkyl of from one to six carbon atoms" as used herein is meant branched and unbranched hydrocarbon groups containing from one to six carbon atoms including, for example, methyl, ethyl, n- and iso-propyl, n-, sec-, iso-, and tert-butyl, n-, sec-, iso-, and neopentyl, etc.

Further included in the scope of the present invention are compounds in which the acetic or propanoic acid side chain is converted to an amide function by reaction with a pharmaceutically acceptable amine. Preferred amines for this purpose are selected from the mono- and dialkylamines containing from one to six carbon atoms, particularly methylamine ethylamine, dimethylamine, diethylamine, and the group consisting of N,N-diisopropylaminoethylamine, N',N'-diisopropylaminoethylamine, 2,6-dimethylaniline, 2,6-dimethylpiperidinylethylamine, 4-aminopyridine, 3,4-diaminopyridine, substituted on either the 3- or 4-amine nitrogen.

The invention further contemplates compounds in which the nitrogen atom of the lactam ring is derivatized with an unsubstituted, monosubstituted, or disubstituted benzoyl group. The benzoyl group, if substituted, is preferably substituted with halogen, particularly, chlorine or fluorine; hydroxyl; alkoxyl of from one to six carbon atoms, particularly methoxyl, ethoxyl; phenoxyl, and phenylmethoxyl; amino; monoalkylamino or dialkylamino of from one to six carbon atoms, particularly methyl or dimethylamino; or methylenedioxy.

The acidic compounds of the present invention (structure I where $R_1$ is hydroxyl) form salts with pharmaceutically acceptable metal or amino cations derived from organic and inorganic bases. The term "pharmaceutically acceptable metal cation" contemplates positively charged metal ions such as those derived from sodium, potassium, calcium, magnesium, iron, zinc, and the like.

The term "pharmaceutically acceptable amine cation" contemplates the positively charged ions derived from ammonia and organic nitrogenous bases strong enough to form such cations. Bases useful for the formation of pharmaceutically acceptable nontoxic acid addition salts of compounds containing a carboxyl acid function form a class whose limits are readily understood by those skilled in the art. Merely for illustration, this class of amines can be said to comprise, in cationic form, those of the formula:

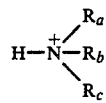

$R_a$, $R_b$, and $R_c$ independently are hydrogen, alkyl of from one to six carbon atoms, cycloalkyl of from about three to six carbon atoms, aryl, aralkyl of from about seven to about ten carbon atoms, hydroxyalkyl of from two to four carbon atoms, or monarylhydroxyalkyl of from about 8 to about 15 carbon atoms. Further, when taken together with the nitrogen atom to which they are attached, any two of Ra, Rb, and Rc may form part of a 5-membered or 6-membered nitrogen heterocyclic aromatic or nonaromatic ring containing carbon or oxygen, said nitrogen heterocyclic rings being unsubstituted, monosubstituted or disubstituted with alkyl groups of from one to six carbon atoms.

Specific examples of organic amine cations contemplated as falling within the scope of the present invention include mono-, di-, and trimethylammonium, mono-, di-, and triethylammonium, mono-, di-, and tripropylammonium (n-propyl and iso-propyl), ethyldimethylammonium, benzylammonium, dibenzylammonium, benzyldimethylammonium, cyclohexylammonium, piperidinium, morpholinium, pyrrolidinium, 4-ethylmorpholinium, 1-isopropylpyrrolidinium, 1,4-dimethylpiperazinium, 1-n-butylpiperdininum, 2-methylpiperidinium, 1-ethyl-2-methylpiperidinium, mono-, di-, and triethanolammonium, ethyldiethanolammonium, n-butylmonoethanolammonium, tris(hydroxymethyl)methylammonium, phenylmonoethanolammonium, and the like.

The ammonium, amine, or metal salts are prepared by reaction of the appropriate acetic or propanoic acid compound of this invention with an equivalent amount of an organic amine base or an inorganic base such as ammonium hydroxide, sodium hydroxide, potassium hydroxide, sodium carbonate, calcium carbonate, sodium bicarbonate, and the like in an appropriate solvent such as water or an aqueous alcohol, followed by removal of the solvent under reduced pressure.

The free acid form of the compound may be regenerated, if desired, by contacting the salt with a dilute aqueous solution of an acid such as hydrochloric acid.

The compounds of this invention are prepared by the methods outlined in Synthetic Schemes 1 or 2 below. Referring to Synthetic Scheme 1, 2,6-alkylacid-disubstituted cyclohexanone or 2,5-alkylacid-disubstituted cyclopentanone compounds of general formula II, where x, y, and Z are independently zero or one, and R and R' are independently hydrogen, alkyl of from one to six carbon atoms or benzyl, are converted to the corresponding oxime Va or alkoxime derivatives, Vb, or the N,N-dimethlyhydrazone derivatives, VI, by reaction with hydroxylamine, IIIa, the corresponding 0-alkyl-substituted alkoxylamine, IIIb (where R" is alkyl of from one to six carbon atoms) or with N,N-dimethylhydrazine, IV.

The starting ketone diesters or diacids (II) are readily produced by the general method discovered by Openshaw and Robinson, *J. Chem. Soc.*, 941 (1937), and applied to cyclopentanone derivatives by Chaterjee, et al., *J. Ind. Chem Soc.*, 17:161 (1940); *Science and Culture*, 6:724 (1941).

Compounds of type V, i.e. oxime diesters, have been prepared as intermediates by Leonard and Middleton, in their synthesis of the totally reduced (non-oxo-containing) tricyclic nitrogen compounds, *J. Amer. Chem. Soc.*, 74: 5114 (1952).

Catalytic reduction of the oxime derivatives V or the N,N-dimethylhydrazone derivatives, VI, by hydrogen over, for example, rhodium/carbon catalyst produces the bicyclic lactam esters VII.

The esters may be employed as such or converted, if desired, to other esters by conventional transesterification reaction, or to the free acids by saponification followed by acidification. The free acids are converted, if desired, by conventional means to the corresponding ammonium, metal, or organic amine salts.

The free acids may be further converted, if desired, to tricyclic diones VIII by cyclization in acetic anhydride, and the resulting tricyclic dione compounds solvolyzed in appropriate alcohols to yield the corresponding bicyclic lactam esters, or hydrolyzed in dilute aqueous acid to produce the bicyclic lactam acids. This reaction sequence is particularly useful in which one of the lactam rings in the tricyclic compound is a five-membered ring and the other is a six-membered. Solvolysis in alcoholic solution, catalyzed by a trace of acid, generally results in the formation of the product in which the smaller five-membered lactam ring is opened.

This reaction sequence is also particularly useful to prepare the benzyl and substituted benzyl esters and the claimed amides when the diones VIII are reacted with the benzyl alcohols with a trace of acid or are reacted with amines to form amides such as IXa or IXb.

The esters of the compounds are converted to the amide derivatives by ammonolysis, aminolysis, or other conventional reactions known to those skilled in the art.

The lactam ring nitrogen atom is substituted with a benzoyl group or a substituted benzoyl group by reaction of benzoyl halide or appropriately substituted benzoyl halide, X, (such as the 4-methoxybenzoyl chloride) with the lactam esters in a suitable solvent, such as tetrahydrofuran under reflux or toluene at 100° C., in the presence of an equivalent amount of a hydrogen ion scavenger, for example, triethylamine to form XI. These benzyl esters, (XI), are of particular value to prepare the compounds with a benzoyl group on the lactam ring nitrogen and the free carboxylic acid, XII, by hydrogenoysis using catalytic hydrogenation, for instance $H_2$ and Pd/C.

SYNTHETIC SCHEME 1

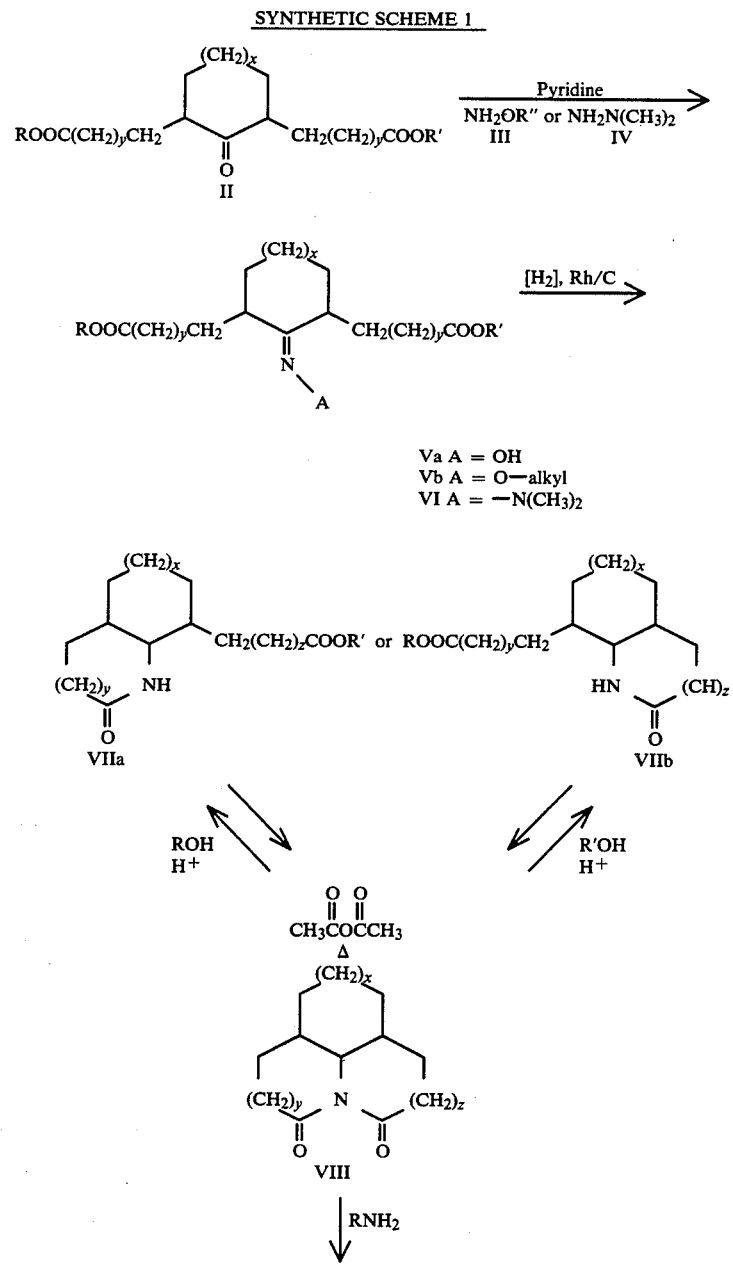

-continued
SYNTHETIC SCHEME 1

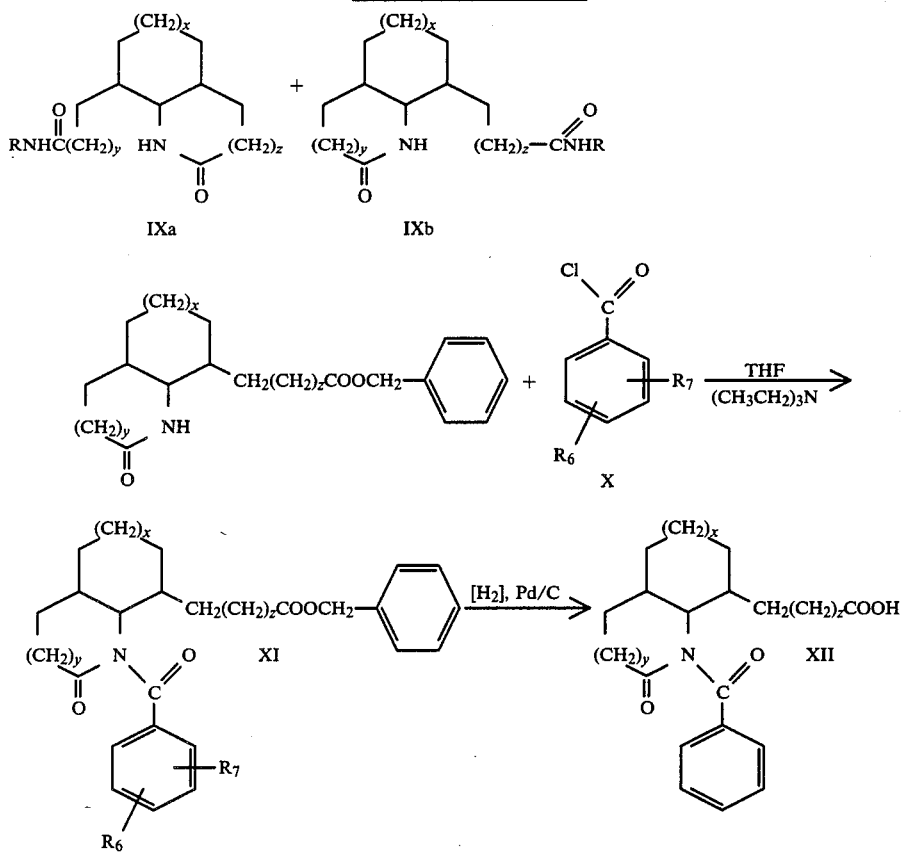

Alternatively, the compounds of the present invention may be prepared by the general methods outlined in Synthetic Sequence 2, typified by reactions where x is two or three.

The known cycloalkanones, XIII (where x=two or three) are reacted with pyrrolidine in the presence of an acid, such as p-toluenesulfonic acid, to produce the enamine condensation products, XIV. The enamines, XIV, are reacted with methyl bromoacetate in a polar solvent such as acetonitrile, containing an acidacceptor such as di-isopropyl-ethylamine to produce the intermediates, XV, which are not isolated. The intermediates when x is two is converted by aqueous acid during work-up to the cycloheptanone-2,7-diacetic acid ester, XVI.

The di-ester, XVI is converted first, by reaction with methoxyamine to the corresponding 0-methyl oxime (which is not isolated, and then subsequently by catalytic hydrogenation to the lactam ester, XVII. Upon ring closure to produce the lactam ring in XVII three isomers are generated, corresponding to the cis or trans relationship of the two carbon atoms and the nitrogen atom attached to the cycloheptane ring.

The lactam ester, XVII, is next saponified in the conventional manner with a dilute aqueous base, such as sodium hydroxide, and then acidified to produce the lactam acid, XVIII, or is converted to other acid derivatives in a manner as detailed above in Synthetic Scheme 1.

Alternatively, intermediate XV is converted to the 0-methyloxime, XIX, by reaction with methoxyamine and subsequently the diester oxime, XIX is reduced catalytically and is converted directly to the lactam acid esters, XX, by conventional saponification followed by acidification to the lactam acids, XXI. As with compound XVIII, there are three isomers of compound XXI corresponding to the cis or trans relationship of the two carbon atoms and the nitrogen atom attached to the cyclooctane ring.

SYNTHETIC SCHEME 2

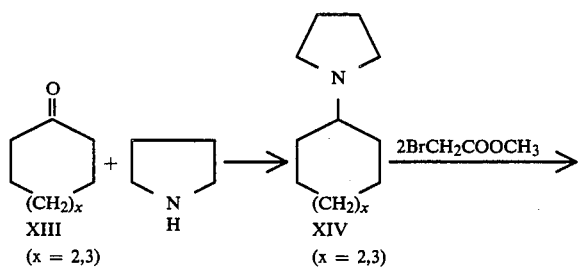

-continued
SYNTHETIC SCHEME 2

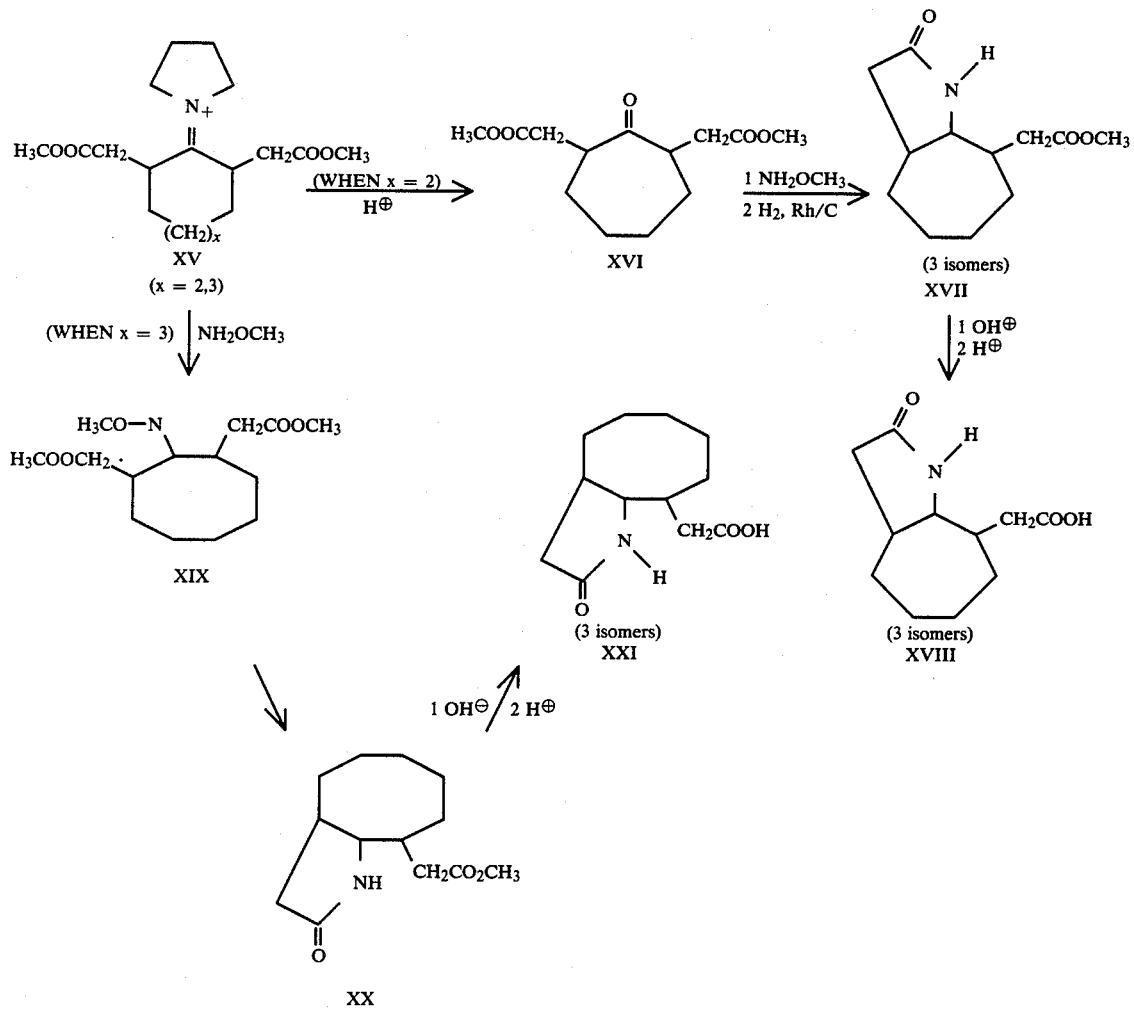

Compounds contemplated as falling within the scope of the present invention include, but are not necessarily limited to, the following examples.
Octahydro-2-oxocyclopenta[b]pyrrole-6-acetic acid.
Octahydro-2-oxo-1H-1-pyrindine-7-acetic acid.
Octahydro-2-oxo-1H-indole-7-acetic acid.
Octahydro-2-oxo-1H-indole-7-propanoic acid.
Decahydro-2-oxo-8-quinolineacetic acid.
Decahydro-2-oxo-8-quinolinepropanoic acid.
Octahydro-2-oxo-cyclopenta[b]pyrrole-6-acetic acid, methyl ester.
Octahydro-2-oxo-1H-indole-7-acetic acid, methyl ester.
Octahydro-2-oxo-1H-indole-7-acetic acid phenylmethyl ester.
Decahydro-2-oxo-8-quinolineacetic acid, methyl ester.
Octahydro-2-oxo-1H-1-pyrindine-7-propanoic acid, 1,1dimethylethyl ester.
Octahydro-1-(3-hydroxy-4-methylbenzoyl)-2-oxo-1H-1-pyrindine-7-acetic acid, methyl ester.
1-Benzoyloctahydro-2-oxo-1H-1-pyrindine-7-propanoic acid, phenyl ester.
1-(4-Fluorobenzoyl)decahydro-2-oxo-7-quinolineacetamide.
1-(2-Chlorobenzoyl)octahydro-N-methyl-2-oxocyclopenta[b]pyrrole-6-acetamide.
Octahydro-1-(3-fluorobenzoyl)-N,N-dimethyl-2-oxo-1H1-pyrindine-7-propanoic acid-7-propanamide.
Octahydro-1-(4-hydroxybenzoyl)-2-oxo-N-4-pyridinyl-1H-indole-7-acetamide.
N-(4-Amino-3-pyridinyl)-octahydro-2-oxocyclopenta[b]-pyrrole-6-propanamide.
Decahydro-2-oxo-cyclohepta[b]pyrrole-8-acetic acid.
Decahydro-2-oxo-1H-cycloocta[b]pyrrole-9-acetic acid.

Also in accordance with the present invention, pharmaceutical compositions may be produced by formulating compounds having structural formula I above in unit dosage form with a pharmaceutically acceptable carrier. Some examples of unit dosage forms are tablets, capsules, lozenges, and pills; as well as powders and aqueous and nonaqueous solutions and suspensions packaged in containers containing either one, or some larger number of dosage units and capable of being subdivided into individual doses by such means as measurement into a teaspoon or other standard container.

Some examples of suitable pharmaceutical carriers, including pharmaceutical diluents, are sugars such as lactose and sucrose; starches such as corn starch and potato starch; cellulose derivatives such as sodium carboxymethylcellulose, ethyl cellulose, methyl cellulose, and cellulose acetate phthalate; gelatin; talc; stearic acid; magnesium stearate; vegetable oils such as peanut oil, cottonseed oil, sesame oil, olive oil, corn oil, and oil of theobroma; propylene glycol; glycerin; sorbitol; polyethylene glycol; water; agar; alginic acid; as well as other compatible substances normally employed in pharmaceutical formulations.

The pharmaceutical compositions of this invention can also contain other components such as coloring agents, flavoring agents, and/or preservatives. These latter materials, if present, are generally used in relatively small amounts. The compositions can, if desired, also contain other therapeutic agents.

The percentage of active ingredient in the foregoing compositions can be varied within wide limits, but for practical purposes, the active ingredient is preferably present in a concentration of a least 10% in a solid composition, and at least 2% in a primarily liquid composition. The most satisfactory compositions are those in which a much higher proportion of the active ingredient is present. The pharmaceutical compositions of this invention preferably contain from 0.1 to 250.0 mg, preferably from 1 to 25 mg of the active ingredient per dosage unit so that the entire amount to be administered during a day can be made from a reasonable number of dose units.

The compounds of the present invention may exist as solids in anhydrous form as well as forms which are solvated with water, alcohols, and other pharmaceutically acceptable solvents. These solid forms may be incorporated into formulations intended for parenteral administration. Such formulations may be either in solution form or in powdered form intended for combination with an isotonic solution containing other ingredients such as preservatives, etc.

The solid forms of the compounds of this invention may also be incorporated into suppository formulations intended for rectal administration or into syrup formulations intended for oral administration.

The mammalian dose range for a 70 kg subject is from 1 to 1500 mg of compound per kg of body weight per day, optionally administered in portions.

The compounds of the present invention are useful for treating senility or for reversing amnesia. The effectiveness of these compounds was evaluated by a test designed to show the ability of a given substance to reverse amnesia induced by electroconvulsive shock. The test is more fully described in U.S. Pat. No. 4,154,347, issued Mar. 20, 1979, and incorporated herein by reference. The only differences between the tests conducted in the present case and that described in the referenced patent were that in the present case, the test compounds were administered orally and the duration of the electrical shock used to induce amnesia in the test animals was 1.0 second.

The data from tests conducted with representative compounds of the present invention appear in the following Table. The following criteria were used in interpreting the data: 40% or more amnesia reversal in the test animals=active, A; 25% to 39% amnesia reversal=borderline activity, C; 0% to 24% reversal of amnesia=inactive, N.

TABLE

| | | | | | | | | | |
|---|---|---|---|---|---|---|---|---|---|
| | | | | | Percent Amnesia Reversal of Orally Administered Test Compounds | | | | |
| | | | | | Dose (mg/kg of Body Weight) | | | | |
| Compound | x | y | z | $R_1$ | $R_2$ | 100 | 10 | 1 | 0.1 | 0.01 |
| 1 | 0 | 0 | 0 | —OH | H | 12 (N) | 37 (C) | 50 (A) | — | — |
| 2 | 0 | 0 | 0 | —OCH$_3$ | H | 14 (N) | 0 (N) | 17 (N) | — | — |
| 3* | 1 | 0 | 0 | —OH | H | 62 (A) | 75 (A) | 75 (A) | — | — |
| 3* | 1 | 0 | 0 | —OH | H | — | — | 21 (N) | 40 (A) | 43 (A) |
| 4** | 1 | 0 | 0 | —OH | H | 48 (A) | 40 (A) | 0 (N) | — | — |
| 5 | 1 | 0 | 0 | —OCH$_3$ | H | 82 (A) | 85 (A) | 36 (C) | — | — |
| 6 | 1 | 0 | 0 | —OCH$_2\phi$ | H | 47 (A) | 47 (A) | 54 (A) | — | — |
| 7 | 1 | 1 | 0 | —OH | H | 38 (C) | 65 (A) | 53 (A) | — | — |
| 8 | 0 | 1 | 0 | —OH | H | 38 (C) | 75 (A) | 46 (A) | — | — |
| 9 | 0 | 0 | 1 | —OH | H | — | 50 (A) | 89 (A) | 72 (A) | — |
| 10 | 0 | 1 | 1 | —OH | H | 78 (A) | 22 (N) | 54 (A) | — | — |

*Hydrogen atoms attached to at positions a, b, and c all cis.
**Hydrogen atoms attached at positions a and be cis to one another; hydrogen atom attached at position c trans to those attached at positions a and b.

The following representative examples are provided to enable one skilled in the art to practice the present invention. These examples are merely illustrative of the preparation of compounds in accordance with the present invention and are not to be read as limiting the scope of the invention as defined by the appended claims.

EXAMPLE 1

Preparation of cyclopentanone 2,5-diacetic acid dimethyl ester 0-methyloxime

Cyclopentanone 2,5-diacetic acid (synthesized in J. Ind. Chem. Soc., 17, 161–166 (1947), (20 g (0.1 mol)), in 200 ml of methanol is saturated with gaseous hydrogen chloride. The solution is refluxed for 16 hours and is concentrated under reduced pressure. The residual oil is distilled to yield cyclopentanone 2,6-diacetic acid dimethyl ester with a boiling point of 110°–112° C. at 0.1 mm pressure. Cyclopentanone 2,6-diacetic acid dimethyl ester, 13.4 g (0.058 mol), is dissolved in 125 ml of pyridine and 5.3 g (0.065 mol) of methoxyamine hydrochloride is added portionwise with stirring under an atmosphere of nitrogen. The mixture is stirred 48 hours and diluted with 250 ml of water. The turbid mixture is extracted with five portions of 75 ml of chloroform. The combined extracts are dried over anhydrous magnesium sulfate. The dried extracts are filtered and concentrated to yield a residue of yield cyclopentanone 2,6-diacetic acid dimethyl ester 0-methyloxime (VPC of this material=100% and it was used as such).

Preparation of octahydro-2-oxocyclopenta[b]pyrrole-6-acetic acid (3aα, 6β, 6aα),octahydro-2-oxocyclopenta[b]pyrrole-6-acetic acid (3aα, 6α, 6aα) and corresponding methyl esters A solution of 14.45 grams (0.055 mol) cyclopentanone 2,5-diacetic acid dimethyl ester 0-methyl oxime is dissolved in 140 ml of methanol and is treated with hydrogen using a 10% rhodium on carbon (Rh/C) catalyst at 50 psi (44.7 kPascal) and 50° C. The mixture is filtered and concentrated at reduced pressure to yield a mixture of octahydro-2-oxocyclopenta[b]pyrrole-6acetic acid methyl ester (3aα, 6β, 6aα) and octahydro-2-oxocyclopenta[b]pyrrole-2-oxo-6-acetic acid methyl ester (3aα, 6α, 6aα) and the corresponding acids. The acids can be separated from the esters by chromatography over SiO₂ using 5% 2-propanol in methylene chloride for elution. Fractional crystallization from anhydrous diethylether separates the isomeric esters. Octahydro-2-oxocyclopenta[b]pyrrole-6-acetic acid methyl ester 3aα, 6β, 6aα) has a melting point of 100°-110° C. and octahydro-2-oxocyclopenta[b]-pyrrole6-acetic acid methyl ester (3aα, 6α, 6aα) has a melting point of 60°-100° C.

Hexahydro-2-oxocyclopenta[b]pyrrole-6-acetic acid methyl ester (3aα, 6β, 6aα), 2.2 g (0.011 m), is treated with 11 ml of 1N sodium hydroxide solution with stirring at 50° C. for 15 minutes. The reaction mixture is extracted with diethyl ether and the aqueous layer is passed through a Dowex-acid column. Concentration of the eluate followed by filtration of the crystals yields hexahydro-2-oxocyclopenta[b]pyrrole-2-oxo-6-acetic acid (3aα, 6β, 6aα) with a melting point of 186°-189° C.

Hexahydro-2-oxocyclopenta[b]pyrrole-6-acetic acid methyl ester (3aα, 6α, 6Aα), 2.2 g (0.011 m) is treated with 11 ml of 1N sodium hydroxide solution with stirring at 50° C. for 15 minutes. The reaction mixture is extracted with diethyl ether and the aqueous layer is passed through a Dowex-acid column. Concentration of the eluate followed by filtration to collect the crystalline product yields hexahydro-2-oxocyclopenta[b]pyrrole-6-acetic acid (3aα, 6α, 6aα) with a melting point of 230°-232° C.

EXAMPLE 2

Preparation of cyclohexanone 2,6-diacetic acid dimethyl ester 0-methyloxime

A solution of 20.2 g (0.094 mol) cyclohexanone 2,6-diacetic acid (synthesized in *J. Ind. Chem. Soc.*, 24, 169-172 (1947)) in 200 ml of methanol is saturated with gaseous hydrogen chloride. The solution is refluxed for 16 hours and is concentrated under reduced pressure. The residual oil is distilled to yield cyclohexanone 2,6-diacetic acid dimethyl ester with a boiling point of 115°-120° C. at 0.1 mm pressure. Cyclohexanone 2,6-diacetic acid dimethyl ester 15.8 g (0.065 mol), is dissolved in 125 ml of pyridine and 5.85 g (0.07 mol) of methoxyamine hydrochloride is added portionwise with stirring under an atmosphere of nitrogen. The mixture is stirred 48 hours and diluted with 250 ml of water. The turbid mixture is extracted with 5 portions of 75 ml of chloroform. The combined extracts are dried over anhydrous magnesium sulfate. The dried extracts are filtered, concentrated and the residue distilled to yield cyclohexanone 2,6-diacetic acid dimethyl ester 0-methyloxime with a boiling point of 120°-125° C. at 0.3 mm pressure.

Preparation of octahydro-2-oxo-1H-indole-7-acetic acid methyl ester (3aα, 7β, 7aα) and octahydro-2-oxo-1H-indole-7-acetic acid methyl ester (3aα, 7α, 7aα)

A solution of 11.9 g (0.043 mol) cyclohexanone, 2,6-diacetic acid dimethyl ester 0-methyl oxime is dissolved in 100 ml of methanol and is treated with hydrogen using a 10% rhodium on carbon (Rh/C) catalyst at 53.5 psi and 50° C. The mixture is filtered and concentrated at reduced pressure to yield a mixture of octahydro-2-oxo-1H-indole-7-acetic acid methyl esters (3aα, 7β, 7aα; and 3aα, 7α, 7aα). These can be separated by fractional crystallization using anhydrous diethyl ether into octahydro-2-oxo-1H-indole-7-acetic acid methyl ester (3aα, 7β, 7aα) with a melting point of 145°-148° C. and octahydro-2-oxo-1H-indole-7-acetic acid methyl ester (3aα, 7α, 7aα) with a melting point of 110°-120° C. The latter contained a small amount of the "all cis-isomer."

Preparation of octahydro-2-oxo-1H-indole-7-acetic acid (3aα, 7β, 7aα) and octahydro-2-oxo-1H-Indole-7-acetic acid (3aα, 7α, 7aα)

A solution of 50 ml (0.05 mol) of 1N sodium hydroxide is added to a mixture of octahydro-2-oxo-1H-indole-7-acetic acid methyl esters (3aα, 7β, 7aα; and 3aα, 7α, 7aα) with stirring. The mixture is stirred and heated at 50° C. for 30 minutes. The mixture is cooled and extracted with diethyl ether and the basic aqueous phase is acidified with an equivalent of 2N hydrochloric acid. Alternatively the basic solution can be passed through a Dowex 50W-acid column and the acids isolated by freeze drying the filtrate. The mixture of octahydro-2-oxo-1H-indole-7-acetic acids (3aα, 7β, 7aα and 3aα, 7α, 7aα) has a melting point of 185°-215° C. and can be used as is in the cyclization procedure or separated by fractional crystallization from water. Octahydro-2-oxo-1Hindole-7-acetic acid (3aα, 7β, 7aα) has a melting of 230°-232° C. Octahydro-2-oxo-1H-indole-7-acetic acid (3aα, 7α, 7aα) has a melting point of 240°-242° C.

EXAMPLES 3 AND 4

Preparation of cyclohexanone 2-acetic acid 6-propanoic acid diethyl ester 0-methyloxime Cyclohexanone 2-acetic acid 6-propanoic acid (synthesized in *J. Amer. Chem. Soc.*, 74, 5114 (1952)), 19.4 grams (0.085 mol), is dissolved in 200 ml of ethanol and is saturated with gaseous hydrogen chloride. The solution is refluxed for 16 hours and is concentrated under reduced pressure. The residual oil is distilled to yield cyclohexanone 2-acetic acid 6-propanoic acid diethyl ester. A solution of 56.8 g (0.2 mol) of cyclohexanone 2-acetic acid 6-propanoic acid diethyl ester in 500 ml of pyridine is treated with 21 g (0.25 mol) methoxyamine hydrochloride. The solution is stirred 36 hours and is poured into 1.5 l of water. The turbid mixture is extracted with five portions of 250 ml of chloroform. The combined extracts are dried over anhydrous magnesium sulfate. The extracts are filtered and concentrated to leave a residual oil of cyclohexanone 2-acetic acid 6-propanoic acid diethyl ester 0-methyloxime which is used as such.

Preparation of (4aα, 8β, 8aα) and (4aα, 8α, 8aα) decahydro-2-oxo-8-quinolineacetic acids and ethyl esters A solution of 17.1 g (0.54 mol) cyclohexanone 2-acetic acid, 6-propanoic acid, diethyl ester 0-methyl oxime is dissolved in 170 ml of methanol and is treated with hydrogen using a 10% rhodium on carbon (Rh/C) catalyst at 50 psi (44.7 kPascal) and 50° C. The solution is filtered and concentrated at reduced pressure to yield a mixture of (4aα, 8β, 8aa) and (4aα, 8α, 8aα) decahydro-2-oxo-8-quinoline acetic acid ethyl esters with a melting point of 195°-200° C. These are hydrolyzed by treatment with 1N sodium hydroxide followed by neutralization with 1N hydrochloric acid. Fractional crystallization from water allows separation of the cis-trans-mixture (mp=165°–180° C.) into (4aα, 8β, 8aα) decahydro-2-oxo-8-quinolineacetic acid ("cis") with a melting point of 210°–214° C. and (4aα, 8α, 8aα) decahydro-2-oxo-8-quinolineacetic acid ("trans") with a melting point of 235°–240° C.

EXAMPLE 5

Preparation of cyclohexanone 2,6-dipropanoic acid dimethyl ester O-methyloxime

A solution of 30 g (0.1 mol) of cyclohexanone 2,6-dipropanoic acid diethyl ester (synthesized in *J. Amer. Chem. Soc.*, 89, 217 (1963)) in 500 ml of pyridine is treated with 21 g (0.25 mol) methoxyamine hydrochloride. The solution is stirred 36 hours and poured into 1.5 l of water. The turbid mixture is extracted with five portions of 250 mg of chloroform. The combined extracts are dried over anhydrous magnesium sulfate. The extracts are filtered and concentrated to leave a residual oil of cyclohexanone 2,6-dipropanoic acid diethyl ester O-methyloxime which is used as such.

Preparation of (4aα, 8β, 8aα) decahydro-2-oxo-8-quinolinepropanoic acid and ethyl ester ("cis")

A solution of 62.7 g (0.19 mol) of cyclohexanone 2,6-dipropanoic acid diethyl ester O-methyloxime in 630 ml of ethanol is treated with hydrogen using 10% rhodium on C at 50 psi (44.7 kPascal) and 50° C. The mixture is filtered and concentrated at reduced pressure to yield (4aα, 8β, 8aα) decahydro-2-oxo-8-quinolinepropanoic acid ethyl ester ("cis") with a melting point of 45°–50° C. after recrystallization from anhydrous diethyl ether and n-pentane. (4aα, 8β, 8aα) decahydro-2-oxo-8-quinolinepropanoic acid ethyl ester ("cis"), 5.1 g (0.02 mol), is treated with 1N (0.02 mol) sodium hydroxide with stirring at 50° C. for 20 minutes. The solution is extracted with diethyl ether and the aqueous basic layer is acidified with 20 ml of (0.02 mol) of 1N hydrochloric acid. (4aα, 8β, 8aα) decahydro-2-oxo-8-quinolinepropanoic acid ("cis") crystallizes and after recrystallization from ethanol has a melting point of 163°–164° C.

EXAMPLE 6

Preparation of cyclopentanone 2-acetic 5-propanoic acid dimethyl ester

Cyclopentanone 2-acetic 5-propanoic acid (*J. Amer. Chem. Soc.;* 74, 5114 (1952)), 41.0 g (0.192 mol), is treated with 500 ml of methanol saturated with dry hydrogen chloride gas. The mixture is refluxed for ten hours. The solution is concentrated at reduced pressure and distilled to yield cyclopentanone 2-acetic acid 5-propanoic acid dimethyl ester with a boiling point of 120°–125° C. at 0.15 mm.

Preparation of cyclopentanone 2-acetic 5-propanoic acid dimethyl ester O-methyloxime Cyclopentanone 2-acetic acid 5-propanoic acid dimethyl ester 21.6 g (0.089 m) is reacted with 7.8 g (0.092 m) O-methylhydroxylamine hydrochloride, in 170 ml of pyridine over a 48 hour period with stirring. The reaction mixture is diluted with 250 ml of water and extracted with chloroform. The extracts are dried and concentrated at reduced pressure and the product used as such.

Preparation of (4aα, 7β, 7aα) and (4aα, 7α, 7aα)-octahydro-2-oxo-1H-1-pyrindine-7-acetic acids and methyl esters A solution of 21.7 g (0.081 m) of cyclopentanone 2-acetic acid,5-propanoic acid O-methyloxime dimethyl ester in 250 ml of methanol is treated with hydrogen using a 10% Rhodium on carbon catalyst at 50 psi (44.7 kPascal) and 50° C. The solution is filtered and concentrated at reduced pressure to yield a mixture of (4aα, 7β, 7aα) and (4aα, 7α, 7aα)-octahydro-2-oxo-1H-1-pyrindine-7-acetic acid methyl esters with a melting point of 165°–170° C. The mixture of (4aα, 7β, 7aα) and (4aα, 7α, 7aα)-octahydro-1H1-pyrindine-7-acetic acid methyl esters, 8.2 g (0.03 m) is treated with 40 ml of 1N sodium hydroxide at 50° C. with stirring for 30 minutes. The solution is extracted with diethyl ether and the aqueous layer is acidified with 45 ml of 1N hydrochloric acid. The product is recrystallized from water to yield (4aα, 7β, 7aα) and (4aα, 7α, 7aα)-octahydro-2-1H-1pyrindine-7-acetic acid with a melting point of 180°–185° C.

EXAMPLE 7

Preparation of hexahydropyrrolo[3,2,1-hi]indole-2,4(1H,5H)-dione (5aα, 8aα, 8bα) and octahydro-2-oxo-9H-indole-7-acetic acid (3aα, 7α, 7aα)

A solution of 1.1 g (0.0055 mol) of a mixture of (3aα, 7α, 7aα) and (3aα, 7β, 7aα) forms of octahydro-2-oxo-1H-indole-7-acetic acid (from Example 2) is prepared in 3.0 g of acetic anhydride. The mixture is stirred and refluxed ten minutes. The acetic acid and excess unreacted acetic anhydride is removed at reduced pressure. The residue is treated with anhydrous diethyl ether and the desired hexahydropyrrolo[3,2,1-hi]indole-2,4(1H,5H)dione (5aα, 8aα, 8bα) is isolated as a crystalline solid with a melting point of 123°–125° C. after recrystallization from toluene. The unreacted (3aα, 7α, 7aα) form of octahydro-2oxo-1H-indole-7-acetic acid (the "trans" form) is isolated by evaporation and trituration of the residue with ethyl acetate, with a melting point of 238°–240° C.

Preparation of octahydro-2-oxo-1H-indole-7-acetic acid phenylmethyl ester (3aα, 7β, 7aα)

A solution of 9.5 grams (0.053 mol) hexahydropyrrolo [3,2,1-hi]-indole-2,4(1H, 5H)-dione (5aα, 8aα, 8bα) in 50 ml of benzyl alcohol is treated with four drops of drops of concentrated hydrochloric acid. The solution is heated to 100° C. for 72 hours, cooled, and diluted with 250 ml of anhydrous diethyl ether. A white crystalline precipitate of octahydro-2-oxo-1H-indole-7-acetic acid (3aα, 7β, 7aα) is isolated by filtration with a melting point of 238°–240° C. The filtrate is cooled and octahydro-2-oxo-1H-indole-7acetic acid benzyl ester (3aα, 7β, 7aα). This is purified by chromatography over silica gel using methylene chloride for elution. The eluate is concentrated at reduced pressure. The resulting solid is triturated with anhydrous diethyl ether and filtered. The filtrate is concentrated at reduced pressure to yield octahydro-2-oxo-1H-indole-7-acetic acid benzyl ester (3aα, 7β, 7aα) with a melting point of 89°–90° C.

EXAMPLE 8

Preparation of
decahydro-3H,5H-benzo[ij]-quinolizine-3,5-dione (7aα, 10aα, 10bα)

A solution of 10 g (0.044 mol) of the (4aα, 8β, 8aα) form of decahydro-2-oxo-8-quinolinepropanoic acid from Example 5 is prepared in 50 g of acetic anhydride. The mixture is stirred and refluxed 15 minutes. The acetic acid and unreacted acetic anhydride is removed at reduced pressure and the residue is treated with anhydrous diethyl ether. The residue crystallizes. The desired decahydro-3H,5H-benzo[ij]quinolizine-3,5-dione (7aα, 10aα, 10bα) has a melting point of 95°–97° C. after trituration with anhydrous diethyl ether.

Preparation of decahydro-2-oxo-8-quinolinepropanoic acid benzyl ester (4aα, 8β, 8aα)

A solution of 0.7 g (0.0033 mol) of decahydro-3H,5H-benzo[ij]quinolizine-3,5-dione (7aα, 10aα, 10bα) in 10 ml of benzyl alcohol is treated with one drop of concentrated hydrochloric acid. The solution is heated at 100° C. for 48 hours and is concentrated at reduced pressure (0.1 mm). The residue is triturated with anhydrous diethyl ether to yield crystalline decahydro-2-oxo-8-quinolinepropanoic acid benzyl ester (4aα, 8aβ, 8aα) with a melting point of 101°–102° C.

EXAMPLE 9

Preparation of
octahydro-4H-pyrrolo[3,2,1-ij]-quinoline-2,4(1H)-dione (6aα, 9aα, 9bα) and
octahydro-4H-pyrrolo[3,2,1-ij]-quinoline-2,4(1H)-dione (6aα, 9aβ, 9bβ)

A solution of 3.3 g (0.015 mol) of a mixture of (4aα, 8α, 8aα) and (4aα, 8β, 8aα) forms of decahydro-2-oxo-8-quinolineacetic acids is prepared in 15 g of acetic anhydride. The mixture is stirred and refluxed ten minutes. The unreacted acetic acid and acetic anhydride is removed at reduced pressure and the residue is treated with anhydrous diethyl ether. The residue crystallizes. The all cis product:octahydro-4H-pyrrolo[3,2,1-ij]-quinoline-2,4(1H)-dione (6aα, 9aα, 9bα) with a melting point of 133°–135° C. is isolated by trituration of the residue with anhydrous diethyl ether. The residual product containing mostly octahydro-4H-pyrrolo[3,2,1-ij]quinoline-2,4(1H)-dione (6aα, 9aα, 9bβ) is purified by chromatography using Silica gel on a Lobar column (elution with ethyl acetate) to yield pure octahydro-4H-pyrrolo[3,2,1-ij]quinoline2,4(1H)-dione (6aα, 9aα, 9bβ) with a melting point of 118°–120° C.

Preparation of octahydro-2-oxo-1H-indole-7-propanoic acid (3aα, 7β, 7aα)

A solution of 0.15 g (0.0007 mol)octahydro-4Hpyrrolo [3,2,1-ij]-quinoline-2,4(1H)-dione (6aα, 9aα, 9bα) in 1 ml of water is treated with 0.7 ml of 1N sodium hydroxide solution. The solution is stirred one hour and is passed over a 2 g Dowex-H+ column. The eluate is concentrated at reduced pressure and the solid is recrystallized from ethanol to yield crystalline octahydro-2-oxo-1H-indole-7-propanoic acid (3aα, 7β, 7aα) with a melting point of 180°–181° C.

EXAMPLE 10

Synthesis of Cycloheptanone 2,7-diacetic acid dimethyl ester

A solution of cycloheptanone pyrrolidine enamine (10.0 g, 0.06 mol), di-isopropylethylamine (23.3 g, 0.18 mol) in freshly distilled acetonitrile (150 ml) is treated dropwise with methyl bromoacetate (27.5 g, 0.18 mol). The mixture is stirred at reflux for 88 hours, concentrated and partitioned between water (150 ml) and chloroform (5×150 ml). The combined chloroform extracts are dried (MgSO$_4$), concentrated, and distilled to yield cycloheptanone 2,7-diacetic acid dimethyl ester, bp 123°–125° C. at 0.6 mm.

NMR (CDCl$_3$) δ1.31–2.05 (br. m., 8H), 2.12–3.45 (m, 6H), 3.32 (s, 6H).

Synthesis of Cycloheptanone 0-methyloxime 2,7-diacetic acid dimethylester

A solution of cycloheptanone 2,7-diacetic acid dimethyl ester (66.8 g, 0.26 mol) and methoxyamine hydrochloride (21.7 g, 0.26 mol) in pyridine (300 ml) is stirred at 25° C. for five days and at 55° C. for 24 hours. Additional methoxyamine hydrochloride (10.8 g, 0.13 mol) is added and the mixture is heated at 80° C. for 18 hours. The solution is poured into water (1 l) and extracted with chloroform (5×250 ml) The extracts are dried (MgSO$_4$) filtered and concentrated at reduced pressure.

The product is purified by flash chromatography on silica gel (elution with hexane:ethyl acetate 4:1).

NMR (CDCl$_4$) δ1.21–1.96 (br. m., 8H), 2.15–2.95 (m, 6H), 3.27 (s, 3H), 3.37 (s, 6H).

Synthesis of ±Cyclohepta[b]pyrrole-8-acetic acid,
decahydro-2-oxo-, (3aα, 8β, 8aα)-;
±Cyclohepta[b]pyrrole-8-acetic acid,
decahydro-2-oxo-, (3aα, 8α, 8aα)-;
±Cyclohepta[b]pyrrole-8-acetic acid,
decahydro-2-oxo-, (3aα, 8β, 8aβ)-and methyl esters A solution of cycloheptanone 0-methyloxime 2,7-diacetic acid methyl ester (58.1 g, 0.18 mol) in methanol (500 ml) is treated with 10% Rh/C (5 g) and hydrogen gas at 50 psi (44.7 kPascal). After the hydrogen gas absorption is completed, the solution is filtered and concentrated to yield the product as an oily solid. The oily solid is triturated with anhydrous diethyl ether and filtered. The mixture of the three methyl ester products had mp 129°–134° C.

NMR (CDCl$_3$) δ1.24–1.85 (br. m., 8H), 2.00–2.62 (m, 5H), 2.63 (m, ½H), 2.83 (m, ½H), 3.22 (br. t., 0.05H, J=(Hz), 3.52 (dd, 0.8H, J=10 Hz, 8 Hz), 3.83 (dd, 0.45H, J=9 Hz, 2.3 Hz), 5.81 (br. s., 0.05H), 6.43 (br. s., 0.5H), 6.65 (br. s., 0.45H).

A mixture of ±cyclohepta[b]pyrrole-8-acetic acid, methyl ester, decahydro-2-oxo-, (3aα, 8β, 8aα)-; ±cyclohepta[b]pyrrole-8-acetic acid, methyl ester, decahydro-2-oxo-, (3aα, 8α, 8aα)-; ±cyclohepta[b]pyrrole-8-acetic acid, methyl ester, decahydro-2-oxo-, (3aα,8β, 8aβ)- (5 g, 0.022 mol) and 2N sodium hydroxide solution (11 ml) is stirred until hydrolysis is complete (TLC). The solution is treated with 2N hydrochloric acid (11 ml) and cooled in a refrigerator. The acid products as a white solid are removed by filtration and dried in vacuo, mp 178°–192° C.

NMR (DMSO, d$_6$) δ1.17–2.64 (br. m., 14H), 3.40 (m, 0.1H), 3.57 (dd, 0.6H, J=10 Hz, 5 Hz), 3.73 (br. d., 0.3H, J=10 Hz), 7.41 (br. s., 0.3 H), 7.67 (br. s., 0.6H), 7.76 (br. s., 0.1H).

Synthesis of
2H-cyclohepta[gh]pyrrolizine-2,4(1H-dione, octahydro-, (5aα, 9aα, 9bα)-;
±2H-cyclohepta[gh]pyrrolizine-2,4(1H)-dione,octahydro-,(5aα, 9aβ, 9bα)-;
2H-cyclohepta[b]pyrrolizine-2,4(1H)-dione, octahydro-,(5aα, 9aα, 9bβ)

A solution of ±cyclohepta[b]pyrrole-8-acetic acid, decahydro-2-oxo-, (3aα, 8β, 8aα)-, ±cyclohepta[b]pyrrole-8-acetic acid, decahydro-2-oxo-, (3aα, 8α, 8aα)- and cyclohepta[b]pyrrole-8-acetic acid, decahydro-2-oxo-, (3aα, 8β, 8aβ) - (8.16 g, 0.039 mol) in acetic anhydride (35 ml) is refluxed for 30 minutes and allowed to stand at room temperature 72 hours. The solution is concentrated at reduced pressure and triturated with anhydrous diethyl ether. Recrystallization (n-heptane) yields a mixture of 2H-cyclohepta[gh]pyrrolizine-2,4(1H)-dione, octahydro-, (5 aα, 9 aα, 9 bα)-; 2H-cyclohepta[gh]pyrrolizine2,4(1H)-dione, octahydro-, (5aα, 9aβ, 9bα)-; ±2H-cyclohepta[gh]pyrrolizine-2,4(1H)-dione,octahydro-, (5aα, 9aα, 9bβ) with mp 80°-87° C.

NMR (CDCl₃) δ1.23-1.76 (br. m., 6H), 1.90-2.07 (m, 3H), 2.22-2.40 (m, 2H), 2.47-2.61 (m, 1H), 2.65-2.74 (m, 1H), 2.88 (dd, 1H, J=17.3 Hz, 7.9 Hz), 3.80 (br. t., 0.1 H, J=10 Hz), 4.01 (br. t., 0.6H, J=9.8 Hz), 4.52 (t., 0.3H, J=6.2 Hz).

EXAMPLE 11

Synthesis of cyclooctanone O-methyloxime 2,8-diacetic acid dimethyl ester

A solution of cyclooctanone pyrrolidine enamine (68.1 g, 0.38 mol); and di-isopropylethylamine (147.3 g, 1.14 mol) in freshly distilled acetonitrile (500 ml) is treated dropwise with methyl bromoacetate (174.3 a, 1.14 mol) and the mixture is stirred and refluxed for 18 hours. A solution of methoxyamine hydrochloride (33.4 g, 0.4 mol.) in pyridine (200 ml) is added.

The solution is stirred at room temperature for two hours. The solution is poured into water (500 ml) and extracted with diethylether (5×500 ml). The combined extracts are dried (MgSO₄), filtered, and concentrated to yield crude cyclooctanone O-methyloxime 2,8-diacetic acid dimethyl ester that is used as is.

Synthesis of ±1H-cycloocta[b]pyrrole-9-acetic acid methyl ester, decahydro-2-oxo-, (3aα, 9β, 9aα)-;
±1H-cycloocta[b]pyrrole-9-acetic acid methyl ester, decahydro-2-oxo-, (3aα, 9β, 9aβ)-;
±1H-cycloocta[b]pyrrole-9-acetic acid methyl ester, decahydro-2-oxo-, (3aα, 9α, 9aα)

A solution of cyclooctanone O-methyloxime 2,8-diacetic acid dimethyl ester (44.9 g, 0.15 mol) in methanol (500 ml) is treated with 10% Rh/C (20 g) and hydrogen gas at 50 psi (44.7 kPascal). After hydrogen uptake is completed the solution is filtered to remove the catalyst and concentrated at reduced pressure. The resulting oil is chromatographed on silica gel (elution with chloroform:isopropanol; 97:3) to yield ±1H-cycloocta[b]pyrrole-9-acetic acid methyl ester, decahydro-2-oxo-, (3aα, 9β, 9aα), ±1H-cycloocta[b]pyrrole-9-acetic acid methyl ester, decahydro-2-oxo-, (3aα, 9α, 9aα)-, 1H-cycloocta[b]pyrrole-9-acetic acid methylester, decahydro-2oxo-, (3aα, 9β, 9aβ)- as a white solid that is used as is.

Synthesis of ±1H-cycloocta[b]pyrrole-9-acetic acid, decahydro-2-oxo-, (3aα, 9β, 9aα)-;
±1H-cycloocta[b]pyrrole-9-acetic acid, decahydro-2-oxo-, (3aα, 9α, 9aα)-;
±1H-cycloocta[b]pyrrole-9-acetic acid, decahydro-2-oxo-, (3aα, 9β, 9aβ)

A suspension of ±1H-cycloocta[b]pyrrole-9-acetic acid methyl ester, decahydro-2-oxo-, (3aα, 9β, 9aα)-; ±1H-cycloocta[b]pyrrole-9-acetic acid methyl ester,-decahydro-2-oxo, (3aα, 9α, 9aα)-; 1Hcycloocta[b]pyrrole-9-acetic acid methyl ester, decahydro-2-oxo, (3 aα, 9β, 9aβ) - (3.0 g, 0.013 mol) in 2N NaOH (6.5 ml) is stirred until hydrolysis is complete. The basic solution is treated with 2N HCl (6.5 ml). The solution is cooled and the product is separated by filtration. After drying in vacuo ±1H-cycloocta[b]pyrrole-9-acetic acid,-decahydro2-oxo-, (3aα, 9β, 9aα)-; ±1H-cycloocta[b]pyrrole9-acetic acid, decahydro-2-oxo-, (3aα, 9α, 9aα)-; ±1H-cycloocta[b]pyrrole-9-acetic acid, decahydro-2-oxo(3aα, 9β, 9aβ)- are isolated as a crystalline solid.

Synthesis of cycloocta[gh]pyrrolizine-2,4(1H,5H)-dione,octahydro-, (5aα, 10aα, 10bα)-; ±cycloocta[gh]pyrrolizine-2,4(1H, 5H)-dione,octahydro-, (5aβ, 10aβ, 10bα)-;
cycloocta[gh]pyrrolizine-2,4(1H,5H)-dione,octahydro-, (5aα, 10aβ, 10bα).

A solution of ±1H-cycloocta[b]pyrrole-9-acetic acid,decahydro-2-oxo-, (3aα, 9β, 9aα)-; ±1H-cylooctα[b]pyrrole-9-acetic acid,decahydro-2-oxo, (3aα, 9α, 9aα)-; ±1H-cycloocta[b]pyrrole-9-acetic acid,decahydro-2-oxo-, (3aα, 9β, 9aβ) (2.8 g, 0.012 mol) in acetic anhydride is heated at reflux for 30 minutes and allowed to cool to room temperature overnight. The solution is concentrated at reduced pressure and the resulting solid is triturated with anhydrous diethyl ether. Sublimation (120° C., 0.1 mm) yields cycloocta[gh]pyrrolizine-2,4-(1H,5H)-dione, octahydro-, (5aα, 10aα. 10bα)-; ±cycloocta[gh]pyrrolizine-2,4(1H,5H)-dione, octahydro-, (5aβ, 10aβ, 10bα)-; cycloocta[gh]pyrrolizine-2,4(1H,5H)dione,octahydro-, (5aα, 10aβ, 10bα)- with mp 121°-124° and 132°-134° C.

NMR (CDCl₃) δ1.08-1.99 (br. m., 10H), 2.13-2.72 (br. m., 5H), 2.99-3.16 (m, 1H), 3.78 (t, 0.2H, J=8.7 Hz), 4.07 (dd, 0.5H, J=9.9, 7.7 Hz), 4.54 (t, 0.3H, J=5.3 Hz).

We claim:

1. A compound having the structural formula

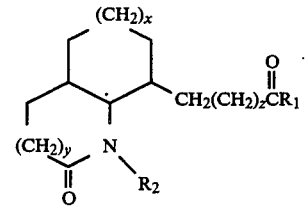

where
x is zero, one, two, or three, y is zero and z is zero or one;
R₁ is selected from
—OH, or pharmaceutically acceptable metal ammonium and amine acid addition salts thereof; and —OR$_3$, where R$_3$ is alkyl of from one to six carbon atoms, phenyl, or benzyl; and R$_2$ is hydrogen.

2. A compound in accordance with claim 1 wherein R$_1$ is —OH or the pharmaceutically acceptable metal, ammonium or amine acid addition salts thereof.

3. A compound in accordance with claim 1 wherein R$_1$ is —OR$_3$ and R$_3$ is alkyl of from one to six carbon atoms, phenyl, or benzyl.

4. The compound in accordance with claim 2 having the name octahydro-2-oxocyclopenta[b]pyrrole-6-acetic acid or the pharmaceutically acceptable salts thereof.

5. The compound in accordance with claim 2 having the name octahydro-2-oxo-1H-indole-7-acetic acid or the pharmaceutically acceptable salts thereof.

6. The compound in accordance with claim 2 having the name octahydro-2-oxo-1H-indole-7-propanoic acid or the pharmaceutically acceptable salts thereof.

7. The compound in accordance with claim 2 having the name decahydro-2-oxo-cyclohepta[b]pyrrole-8-acetic acetic acid or the pharmaceutically acceptable salts thereof.

8. The compound in accordance with claim 2 having the name decahydro-2-oxo-cycloocta[b]pyrrole-9-acetic acid or the pharmaceutically acceptable salts thereof.

9. The compound in accordance with claim 3 having the name octahydro-2-oxo-cyclopenta[b]pyrrole-6-acetic acid methyl ester.

10. The compound in accordance with claim 3 having the name octahydro-2-oxo-1H-indole-7-acetic acid methyl ester.

11. The compound in accordance with claim 3 having the name octahydro-2-oxo-1H-indole-7-acetic acid phenylmethyl ester.

12. A pharmaceutical composition comprising an amount of a compound in accordance with claim 1 effective to reverse electroconvulsive shock-induced amnesia in combination with a pharmaceutically acceptable carrier.

13. A method of reversing electroconvulsive shock-induced amnesia in mammals comprising administering to said mammal an amount of a pharmaceutical composition in accordance with claim 12 effective to reverse electroconvulsive shock-induced amnesia.

* * * * *